United States Patent [19]

Strassmann

[11] Patent Number: 5,453,444
[45] Date of Patent: Sep. 26, 1995

[54] METHOD TO MITIGATE OR ELIMINATE WEIGHT LOSS

[75] Inventor: Gideon Strassmann, Washington, D.C.

[73] Assignee: Otsuka Pharmaceutical Co., Ltd., Tokyo, Japan

[21] Appl. No.: 319,081

[22] Filed: Oct. 6, 1994

Related U.S. Application Data

[63] Continuation of Ser. No. 959,371, Oct. 13, 1992, abandoned.

[51] Int. Cl.$^6$ .................. A61K 31/185; A61K 31/70; A61K 31/715
[52] U.S. Cl. .................. 514/577; 514/25; 514/59
[58] Field of Search .................. 514/577

[56] References Cited

U.S. PATENT DOCUMENTS

| | | | |
|---|---|---|---|
| 4,925,831 | 5/1990 | Durette | 514/49 |
| 4,956,349 | 9/1990 | Beck | 514/54 |
| 5,135,920 | 8/1992 | Kanamaru et al. | 514/59 |
| 5,145,841 | 9/1992 | Cullis-Hill et al. | 514/54 |
| 5,158,940 | 10/1992 | LaRocca et al. | 514/54 |
| 5,162,361 | 11/1992 | Rosenthal et al. | 514/396 |
| 5,173,509 | 12/1992 | Walther et al. | 514/597 |

FOREIGN PATENT DOCUMENTS

| | | | |
|---|---|---|---|
| 0486809 | 5/1992 | European Pat. Off. | 514/577 |

OTHER PUBLICATIONS

Ndung'u et al., J. of Small Aminal Practice, vol. 32, (11), Nov. 1991, pp. 579–584.
Damle et al., "GMP–140 (P–selectin/CD62) binds to chronically chronically stimulated but not resting CD4+ T lymphocytes and requlates their production of proinflammatory cytokines," Eur. J. Immunol. 22:1789–1793 (1992).
Rainsford, "Effects of anti–inflammatory drugs and agents that modify intracellular transduction signals or metabolic activities in inflammatory cells on interleukin–1 induced cartilage proteoglycan resorption in vitro," Pharmacol Res. 25(4) 335–346 (1992).
Hirano et al., Pro. Natl'. Acad. Sci., 84:228 (1987).
Merck Index, 11th Edition, No. 8986. p. 1423 (1989).
Strassmann et al., J. Clin. Invest. 89:1681–1684 (1992).
Hirano et al., Immunol. Today 11:443–449 (1990).
Myers, Am. J. Repro. Immunol. 25:133–136 (1991).
Pollack et al., J. Nat'l. Cancer Inst. 82:(16) 1349–1352 (1990).
Bojanowski et al., Proc. Nat'l. Acad. Sci. 89:3025–3029 (1992).
Baghdiguan et al., Cancer Letters 60:213–219 (1991).
Liu et al., J. Urol. 145:389–392 (1991).
Jentsch et al., J. gen. Virol. 68:2183–2192 (1987).
Strassmann et al., J. Immunol. 148:(11) 3674–3678 (1992).
Gershenwald et al., Proc. Nat'l. Acad. Sci. 87:4966–4970 (1990).
Proceedings of the American Association for Cancer Research, vol. 32 Mar. 1991, p. 55, No. 325.
Proceedings of the American Association for Cancer Research, vol. 30 Mar. 1989, p. 545, No. 2170.

*Primary Examiner*—Jerome D. Goldberg
*Attorney, Agent, or Firm*—Finnegan, Henderson, Farabow, Garrett & Dunner

[57] ABSTRACT

The present invention relates to methods for treating cachexia in a patient and inhibiting IL-6 bioactivity. This is accomplished by administering to a patient an effective amount of a sulfate-containing compound, for example, suramin, a derivative of suramin, Pentosan polysulfate, or Dextran sulfate. The present invention is also effective in combating IL-6 related diseases.

6 Claims, 6 Drawing Sheets

METHOD TO MITIGATE OR ELIMINATE WEIGHT LOSS

This application is a continuation of application Ser. No. 07/959,371, filed Oct. 13, 1992, now abandoned.

FIELD OF THE INVENTION

The present invention relates to a method for treating cachexia in a patient, particularly a human being, and a method for the inhibition of IL-6 activity.

BACKGROUND OF THE INVENTION

Cachexia, a potentially lethal syndrome afflicting mammals, frequently complicates the treatment of infection, inflammation and cancer. It is characterized by profound weight loss caused by wasting of body fat (adipose) and muscle (protein). Tracey et al., *J. Exp. Med.*, Vol. 167, 1211–1227 (March 1988). Lawson et al., *Ann. Rev. Nutr.*, 2:277–301 (1982). Anorexia, anemia, and weakness may also occur in cachexia. Tracey et al., supra. Cachexia may further be characterized by, inter alia, depression of glucose level (hypoglycemia) and elevation of triglyceride level (hypertriglyceridemia).

Cachexia may result from diverse causes such as age, cancer, and infections by parasites and by microorganisms such as bacteria, fungi, viruses and protozoa. Both acute and chronic infections or illnesses frequently cause cachexia. In fact, most chronic, fatal, nonneoplastic diseases terminate in cachexia (e.g. chronic disseminated infections, or prolonged insufficiency of heart, lungs, liver, kidneys, or the small intestines). Lawson et al., *Ann. Rev. Nutr.*, 2:277–301 (1982). Moreover, the syndrome is not alleviated by adequate caloric uptake. Indeed, weight loss may continue in cachexia even while an adequate diet is consumed. Silva et al., *J. General Microbiology*, Vol. 134, 1629–1633 (1988).

Researchers have studied cachexia induced by microbial infections, and by parasitic infections such as trypanosomiasis and leishmaniasis. Sherry et al., J. Cell Biology, Vol. 107, 1269–1277 (October 1988). The study of cachexia induced by microbial infections has shown that the syndrome may result from either the direct effect of the microorganism or from a toxin produced by the microorganism. For example, weight loss has been observed as a toxic manifestation in mice upon injection with endotoxin, the lipopolysaccharide (LPS) derived from gram-negative bacteria. Vogel et al., *Infection and Immunity*, Vol. 56, No. 10, 2650–2657 (October 1988).

Indeed, the toxin produced by a microorganism has been used to create a model for the study of cachexia. In this regard, cachexia has been induced by intraperitoneal injection into mice of trehalose dimycolate (TDM) isolated from *Nocardia asteroides*. Silva et al., *J. General Microbiology*, Vol. 134, 1629–1633 (1988). Researchers have studied the mechanism by which TDM, also known as cord factor (CF), a toxic glycolipid from mycobacteria, induces cachexia. Silva et al., *Infection and Immunity*, Vol. 56, No. 12, 3067–3071 (December 1988). That laboratory observed that administration of CF markedly reduced body weight: the animals became severely wasted and exhibited hypertriglyceridemia, hypoglycemia, and high levels of tumor necrosis factor in plasma. Dexamethasone was found to partially inhibit the cachexia-inducing action of CF.

Recent research has focused on the physiology related to cachexia. For example, the increase in circulating triglycerides observed has been attributed to systemic suppression of lipoprotein lipase (LPL). Tracey et al., *J. Exp. Med.*, Vol. 167, 1211–1227 (March 1988). It has been reported, however, that transplantable adenocarcenoma of the colon (MAC16) produces cachexia symptoms without concomitant hypertriglyceridemia. Mahony et al., *Br. J. Cancer*, 57, 385–389 (1988).

It has also been suggested that tumor necrosis factor, hereinafter "TNF" also known as "cachectin", Beutler et al, *Advances in Immunology*, Vol. 42, 213–231 (1988), may play a central role in cachexia. Tracey et al., *J. Exp. Med.*, Vol. 167, 1211–1227 (March 1988). Michie et al., *Surgery*, Vol. 104, No. 2, 280–286 (August 1988), reports that TNF may represent the primary stimulus that initiates many of the metabolic responses associated with sepsis and endotoxemia.

The role of TNF, however, is not clear. Although cachexia in cancer patients has been associated with the presence of TNF, this factor has not been uniformly detectable in the serum of cachectic patients with cancer. Sherry et al., *The FASEB J.*, Vol. 3, 1956–1962 (June, 1989). In one study, using both cachexia-inducing (MAC16) and non-cachexia-inducing (MAC13) adenocarcinomas, researchers concluded that weight loss produced by TNF arises from an anorexic effect that differs from the complex metabolic changes associated with cancer cachexia. Mahony et al., *Br. J. Cancer*, 57, 385–389 (1988). Similarly, in a study on viral-related cachexia, using mice infected persistently with lymphocytic choriomeningitis virus (LCMV), the laboratory concluded that the greater than 20% cachexia-like weight loss observed was apparently not associated with a measurable increase in TNF. Lathey et al., *Am. J. Pathol.*, 132(3):586–92 (September 1988).

The severe weight loss and debilative wasting of lean body mass of cachexia frequently complicates the treatment of patients suffering from malignancy or chronic infection. Indeed, cachexia contributes to cancer mortality. Some data indicate that as many as 30% of cancer patients die from cachexia, rather than tumor burden. Tracey et al., supra. One medical textbook notes that:

"[t]he most common way in which malignancy leads to death is cachexia: the development of progressive weakness, weight loss, and wasting. Usually, there is a close correlation between the amount of malignant disease present and the severity of cachexia... In this weakened state, cancer patients are particularly susceptible to terminal infections, such as pneumonia, which often precipitates death." van Eys, *Ann. Rev. Nutr.*, 5:435–61 (1985) (based on the second edition of Robbins' Textbook of Pathology).

The severity of cachexia may be unrelated to tumor size or parasite load, and profound wasting has been observed in patients with tumor burdens of only 0.01 to 5.0% body mass. If not reversed, physiological changes associated with cachexia lead to immunological deficiencies, organ failure, and multiple metabolic abnormalities. Tracey et al., *J. Exp. Med.*, 167, 1211–1227 (March 1988). Theologides, *Cancer*, May Supplement, 43, 2004–2012 (1979).

The physiological changes due to cachexia decrease the patient's tolerance to chemotherapy and radiation therapy, as well as increase the frequency of post-surgical complications. The nausea, vomiting, and anorexia induced by chemotherapeutic agents as well as radiation injury can be very severe. In addition, chemotherapy is a major factor in malnutrition. It is well recognized that therapy is often as debilitating as the cancer itself. The malnourished patient has a much narrower safe therapeutic margin for most oncologic therapy. van Eys, Supra.

Further, median survival has been found to be significantly shorter in patients who had lost weight with most types of tumor examined. Lawson et al., *Ann. Rev. Nutr.*, 2:277–301 (1982).

The precise mechanisms by which the cachexia syndrome may cause death in some patients and perhaps contribute to it in others are not completely understood. Lawson et al., *Ann. Rev. Nutr.*, 2:277–301 (1982). Thus, the art has continued to search for effective methods for treating cachexia resulting from etiologies such as cancer or infectious diseases.

SUMMARY OF THE INVENTION

The present invention provides a method for treating cachexia, comprising the step of administering to a patient an amount of a sulfate-containing compound, such as suramin or a derivative thereof, effective for said treatment.

The invention contemplates treating all forms of cachexia, whether induced by infection, cancer, age or otherwise.

The present invention also provides a method for the inhibition of interleukin 6 ("IL-6") activity, comprising the step of administering to a patient an amount of a sulfate-containing compound, such as suramin or a derivative thereof, effective for said inhibition.

Additional objects and advantages of the present invention will be set forth in part in the description which follows. It is to be understood that the general description above and the following detailed description are exemplary and explanatory only and do not limit the present invention, as claimed.

DETAILED DESCRIPTION OF THE INVENTION

The instant invention provides a method for treating cachexia resulting from infection, cancer, age or otherwise.

The claimed method can also be used to treat any of the symptoms associated with the cachexia syndrome. Thus, the method of the instant invention may be employed to mitigate or completely eliminate weight loss due to wasting of body fat and muscle, hypertriglyceridemia, hypoglycemia, and anorexia. In addition, the claimed invention may be used to prevent loss of tissue in vital organs. The instant method is particularly useful in treating cachexia due to cancer or chronic infections.

The method of the instant invention may be used, for example, to treat cachexia arising as a result of infection, chronic or otherwise, caused by a unicellular or multicellular parasite, or microbe such as a bacteria, fungus, protozoa or virus, or a combination of these organisms. For example, the present invention contemplates treatment of cachexia due to:

infections by gram-negative or gram-positive bacteria, such as gram-positive cocci (pneumococcal, staphylococcal and streptococcal infections), infections due to gram-negative cocci (meningoccal infections), infections due to enteric gram-negative bacilli (coli-form bacterial infections, typhoid fever, Salmonella infections, Shigella infections, cholera), infections due to bacteria of the Hemophilus group (pertussis, influenza bacillus infections), tuberculosis infections, fungal infections (Candida), spirochetal and rickettsial infections, viral infections (influenza, hepatitis, Sendai, herpes), and infections due to protozoa (malaria, leishmaniasis).

The method of the instant invention is also useful in treating cachexia resulting from cancer. Treatment of cachexia resulting from either a TNF- or non-TNF-producing cancer is within the scope of the instant invention. Thus, for example, all forms of cachexia produced by carcinomas or leukemias are treatable by the instant method. Treatment according to the claimed invention will mitigate or totally eliminate the symptoms of cachexia, such as wasting and other physiological changes. This treatment may allow the patient to better tolerate chemotherapy or radiation therapy, improving the patient's overall prognosis and quality of life.

Further, the present invention inhibits the bioactivity of interleukin 6 ("IL-6"), which is now believed to be a central cause in cachexia and possibly other diseases such as rheumatoid arthritis. (See, Hirano et al., *J. of Immunology Today*, 11:443–449 (1990) and Hirano et al., *Pro. Nat'l. Acad. Sci.*, U.S.A. 84:228 (1987).) The measurement of the bioactivity of IL-6 is known in the art and can be accomplished by a variety of methods including B-9 assay.

Cachexia is treated and the bioactivity of IL-6 is inhibited by the use of sulfate-containing compounds. The sulfate-containing compounds to be used in the present invention can be any sulfate-containing compound which will inhibit the bioactivity of IL-6 and/or will be effective in the treatment of cachexia as described above.

One example of a sulfate-containing compound that is effective in the inhibition of IL-6 bioactivity and is also effective in the treatment of cachexia is suramin.

The suramin used in the present invention is also known as suramin sodium or 8–8'-[Carbonylbis[imino-3,1 -phenylenecarbonylimino(4-methyl-3,1-phenylene)carbonylimino]] bis-1,3,5-naphthalenetrisulfonic acid hexasodium salt. Commercially available suramin is preferred and is known by the tradenames Bayer 205, 309F, Antrypol, Germanin, Moranyl, Naganol, Naganin, and Naphuride Sodium.

Derivatives of suramin can also be used in the present invention. Examples of such derivatives include, but are not limited to, the derivatives described in Baghdiguian et al., *Cancer Letters*, 60 (1991) pp. 213–219 which is incorporated herein by reference. Other examples of effective sulfate-containing compounds include, but are not limited to, Pentosan polysulfate and Dextran sulfate or a combination of sulfate-containing compounds. Any form of a sulfate-containing compound, for example, suramin or derivatives thereof, Dextran sulfate or Pentosan polysulfate, that provides the desired mitigation or total elimination of cachexia or the inhibition of IL-6 activity is contemplated within the present invention.

According to the methods of the instant invention, sulfate-containing compounds, such as suramin or derivatives thereof, Dextran sulfate and Pentosan polysulfate, may be administered to patients in the commercially obtained form, or may be first formulated into pharmaceutical compositions comprising an effective amount of the sulfate-containing compound and one or more pharmacologically acceptable nontoxic carriers, diluents or adjuvants. Such compositions are, for example, in the form of liquid preparations including solution, suspension, and emulsion preparations. Such compositions may also be solid preparations given as is or reconstituted to a liquid for use by addition of a suitable carrier.

Pharmaceutical carriers may be sterile liquids, such as water and the like. Water is a preferred carrier when the pharmaceutical composition is administered intravenously. Saline solutions and aqueous dextrose and glycerol solutions may also be employed as liquid carriers, particularly for injectable solutions. Other suitable pharmaceutical excipients may be used. These compositions can take the form of solutions, suspensions, tablets, pills, capsules, powders, sustained-release formulations and the like. Suitable pharmaceutical carriers are described in "Remington's Pharmaceutical Sciences" by E. W. Martin.

Sulfate-containing compounds of the present invention may be administered in the appropriate form according to methods known to those skilled in the art, such as orally, intravenously, subcutaneously, intracutaneously or intramuscularly. Intravenously is the preferred method of administration.

It is particularly preferred to administer the sulfate-containing compounds of the present invention, such as the suramin or derivatives thereof, according to the methods of the invention before, as well as after, the onset of cachexia or exposure to the factor giving rise to cachexia.

Persons of ordinary skill in the art will be able to determine the dosage of the sulfate-containing compound effective to achieve the objects of the present invention. Dosages selected are those which mitigate or completely eliminate the symptoms associated with cachexia (e.g. weight loss) or dosages which inhibit IL-6 activity, which symptoms are familiar to those skilled in the art. Determination of the appropriate dosages for treatment are routinely made by those of ordinary skill in the art and are within the array of tasks routinely performed by them without undue experimentation. While the amount of the sulfate-containing compound, such as suramin or derivatives thereof, to be given in any form is not limited specifically, and can be determined suitably according to the age and sex of the patient, the degree of disease, etc., the sulfate-containing compound, for example, suramin or derivatives thereof, may be administered, for example, at a dose of about 0.01 g to about 10 g per week, wherein a week is understood to be 5–7 days. The dose may be given once per week or the dose may be divided and given daily, or the dose may be staggered throughout the week, e.g., biweekly, triweekly.

The term "patient" is used herein in its broadest sense to mean mammals, including humans, as well as other mammals such as farm and laboratory animals, for example, horses, cows, dogs, cats, guinea pigs, mice, and rats.

The present invention is further illustrated by the following examples, which are intended solely to exemplify and not to limit the present invention.

EXAMPLE 1

The effects against cachexia using an effective amount of suramin are shown by the example below.

Eleven male mice (CD)2F1 obtained from Charles Rivers Laboratories were weighed and then were inoculated with $0.5 \times 10^6$ C-26.IVX cells derived from the colon adenocarcinoma (by the procedure described in Strassmann et al., *J. Clin. Invest.*, 89, pp. 1681–84 (May 1992) which is incorporated herein by reference). The day of inoculation was identified as day 0 (d0). On days 7 and 13, five of these mice each received intraperitoneally 0.5 ml of PBS (phosphate buffered saline) and the other six mice each received intraperitoneally 200 mg/kg body weight of suramin diluted in 0.5 ml PBS. On day 19, all the mice were sacrificed and the final total weight, the host weight, the tumor weight, epididymal fat, and dry weight were measured. Table 1 sets forth the results. As can be seen from the results, the average percent weight loss for the mice receiving suramin was 12.0±6.0% while with PBS alone the average percent weight loss of the mice was 30.5±4.8 %. Thus, suramin clearly prevented weight loss in comparison to control animals.

TABLE 1

Suramin Blocks C-26 Mediated Cachexia

| Treatment | Initial wt. (g) | Final total wt. (g) | Host's wt. (g) | Tumor wt (g) | % weight loss | Epididymal fat (g) | Dry wt (g) | Serum Glucose (mg/dl) | IL-6 (U/ml) |
|---|---|---|---|---|---|---|---|---|---|
| PBS d7, 13 | 29.6 | 21.5 | 19.8 | 1.71 | 33.1 | 34 | 6.2 | 39 | 194 |
|  | 32.0 | 21.8 | 20.1 | 1.69 | 37.1 | 47 | 6.2 | 29 | 123 |
|  | 27.7 | 20.8 | 19.3 | 1.50 | 30.3 | 0 | 5.7 | 59 | 141 |
|  | 27.5 | 21.5 | 20.7 | 1.82 | 24.7 | 0 | 5.6 | 74 | 189 |
|  | 29.4 | 22.8 | 21.3 | 1.54 | 27.5 | 96 | 5.2 | 21 | 140 |
|  | 29.3 ± 1.8 | 21.7 ± 0.7 | 20.2 ± 0.8 | 1.65 ± 0.13 | 30.5 ± 4.8 | 35 ± 39 | 5.8 ± 0.4 | 44 ± 21 | 158 ± 32 |
| Suramin d7, 13 200 mg/kg | 26.4 | 25.9 | 25.0 | 0.93 | 5.3 | 236 | 7.8 | 128 | 292 |
|  | 28.3 | 25.2 | 23.3 | 1.98 | 17.6 | 62 | 6.5 | 114 | 360 |
|  | 27.1 | 26.2 | 24.2 | 2.08 | 10.5 | 103 | 6.5 | 100 | 310 |
|  | 27.8 | 25.5 | 23.5 | 1.96 | 15.4 | 105 | 6.6 | 110 | 535 |
|  | 28.4 | 25.4 | 23.1 | 2.36 | 18.6 | 123 | 6.4 | 109 | 477 |
|  | 27.2 | 27.4 | 25.8 | 1.64 | 5.1 | 84 | 6.5 | 116 | 328 |
|  | 27.5 ± 0.8* | 26.9 ± 0.8+ | 24.2 ± 1.1+ | 1.82 ± 0.49* | 12.0 ± 6.0+ | 118 ± 61** | 6.7 ± 0.5** | 113 ± 9+ | 384 ± 99Δ |

TABLE 1-continued

| | | Final | | | | | | Serum | |
|---|---|---|---|---|---|---|---|---|---|
| Treatment | Initial wt. (g) | total wt. (g) | Host's wt. (g) | Tumor wt (g) | % weight loss | Epididymal fat (g) | Dry wt (g) | Glucose (mg/dl) | IL-6 (U/ml) |

(CD)2F1 male mice were inoculated with $0.5 \times 10^6$ C-26.IVX cells and d0. On d7 and 13 mice received PBS or suramin I.P. On d19 mice were sacrificed and cachexia markers were measured. Results are expressed as mean ±SD.
Statistics: *Not significant, $^+p < 0.00001$, **$p < 0.02$, $^\Delta p < 0.0004$

EXAMPLE 2

Figure 1:
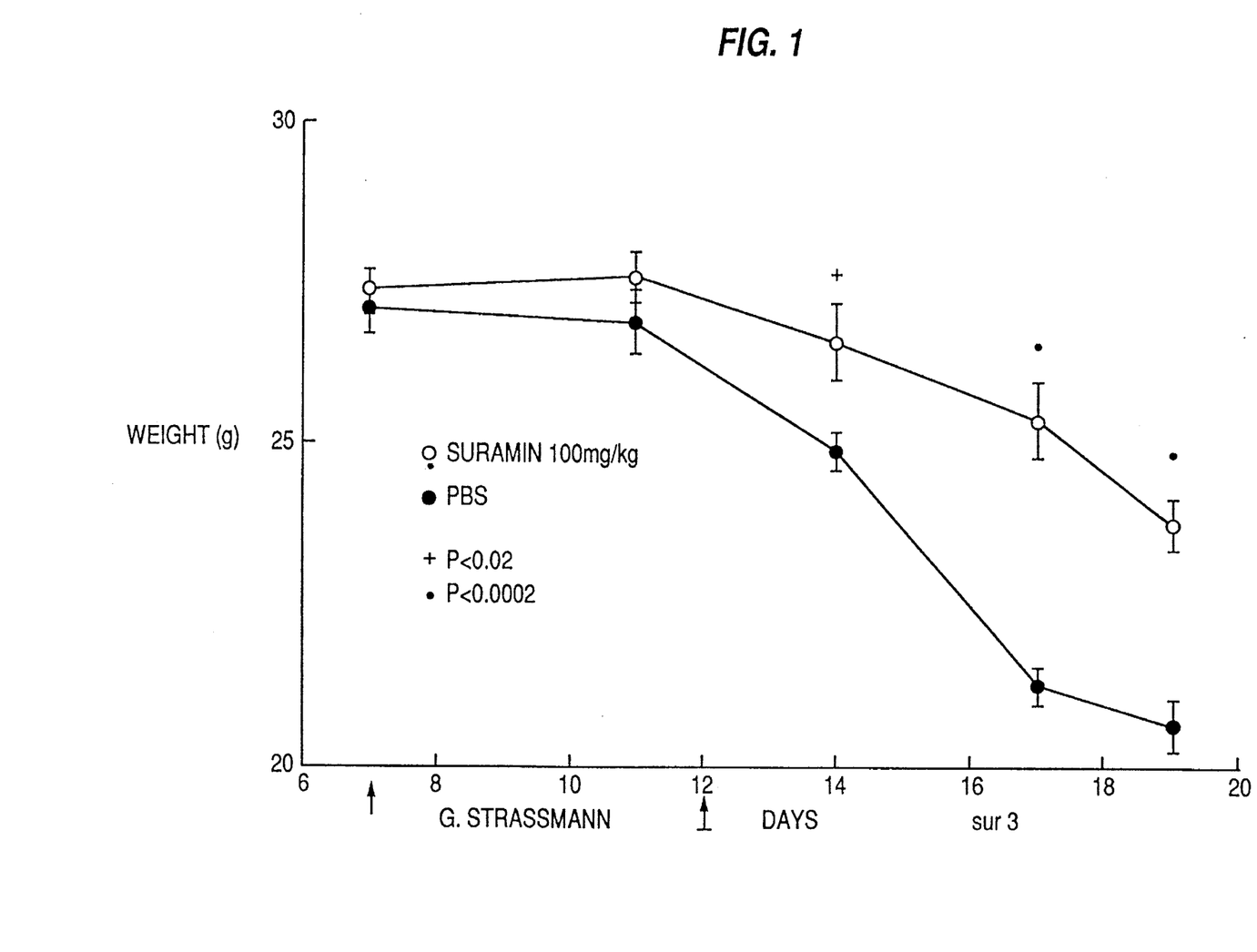
FIG. 1 sets forth the time dependent inhibition of C-26 cachexia with the use of suramin.
Figure 2:
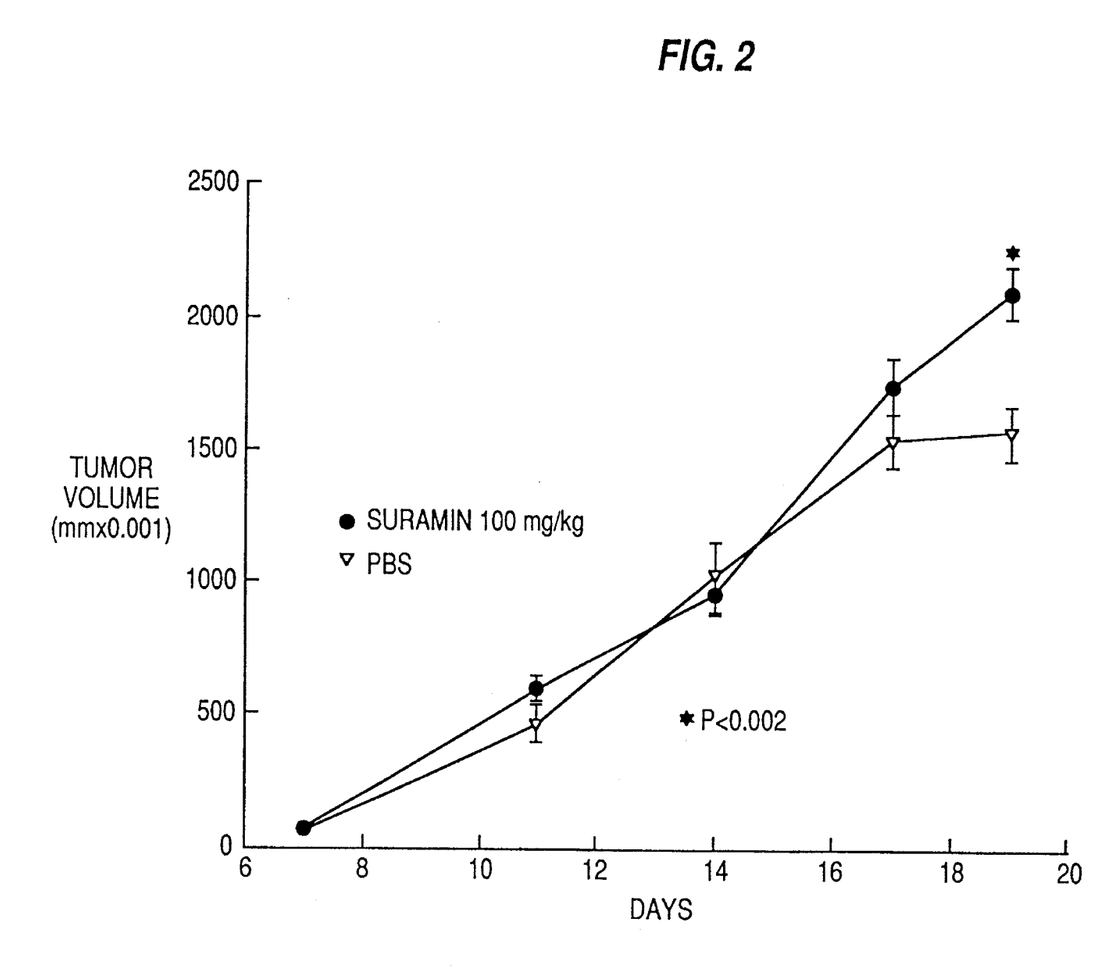
FIG. 2 sets forth the lack of effect of suramin on tumor (C-26) growth in vivo.

In subsequent experiments, eight mice obtained from the same source as above were injected with 0.5 ml PBS intraperitoneally and eight other mice from the same source as above were injected with 100 mg/kg body weight of suramin intraperitoneally. The injections were given on days 7 and 12. The weight of the two groups was measured several times a week. As can be seen in FIG. 1, the suramin inhibited C-26 mediated weight loss in a significant time dependent manner. In the same experiment, tumor volume was also measured and the results are set forth in FIG. 2. As can be seen in FIG. 2, the suramin had no significant effect on the tumor (C-26) growth in-vivo except on day 19. This indicates that the treatment of the present invention affects the host directly.

EXAMPLE 3

Figure 3:
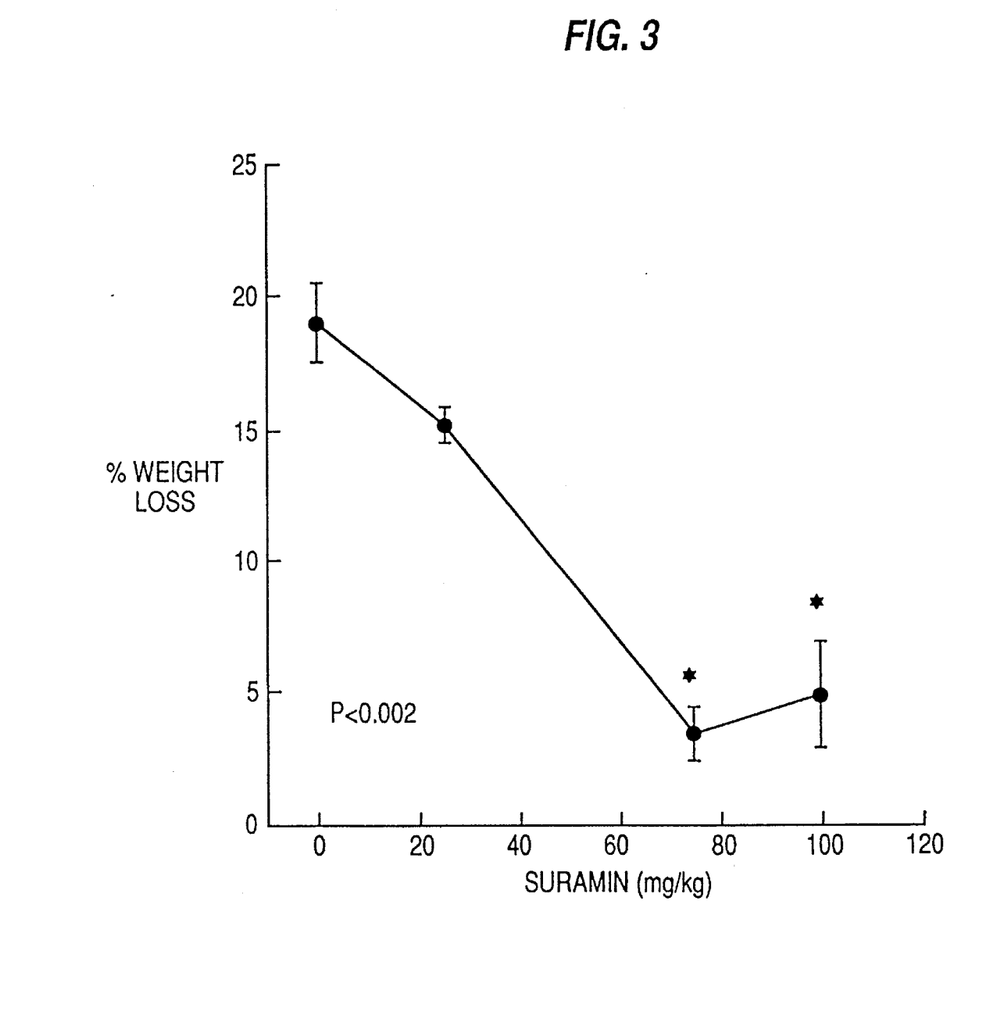
FIG. 3 sets forth the dose dependent inhibition of C-26 cachexia with the use of suramin.

Mice were obtained and injected with C-26 cells as set forth above for Example 1, and then were put into four groups of five mice each. The mice were injected intraperitoneally with increasing amounts of suramin as indicated in FIG. 3 except for the control mice. On day 17, the total weight of each group was compared to a control group of five mice which had been injected with 0.5 ml PBS intraperitoneally. As can be seen in FIG. 3, increasing concentrations of suramin resulted in decreased percentage of weight loss. Thus, suramin inhibited wasting in a dose dependent manner.

EXAMPLE 4

Figure 4:
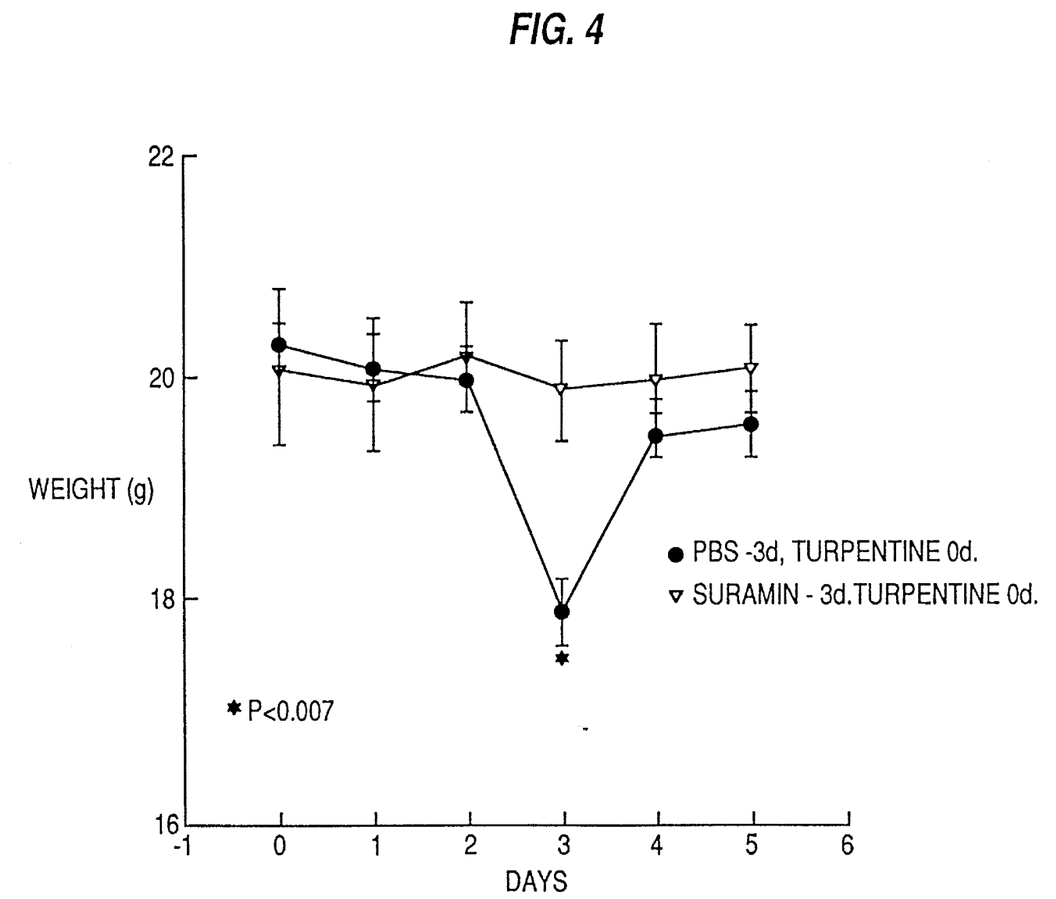
FIG. 4 sets forth the prevention of turpentine-induced wasting with the use of suramin.

FIG. 4 sets forth results of treatment with suramin in the prevention of turpentine-induced wasting, an acute type of inflammation. (See Gershenwald et al., "Interleukin 1 receptor blockade attenuates the host inflammatory response" Proc. Natl. Acad. Sci., 87 4966–70, (July, 1990) for a description of the turpentine-induced wasting procedure). In this experiment, three days before day 0 (day −3), five male (CD)2F1 mice, obtained from Charles Rivers Laboratories, each received intraperitoneally 0.5 ml of PBS. Five other mice obtained from the same source each received intraperitoneally 100 mg/kg body weight suramin diluted with 0.5 ml of PBS. On day 0, all 10 mice received intramuscularly 0.1 ml of turpentine As can be seen in FIG. 4, the mice which received only PBS suffered from an acute reaction to the turpentine which caused a rapid or acute weight loss on day 3. The mice treated with suramin exhibited no such weight loss.

EXAMPLE 5

Figure 5:
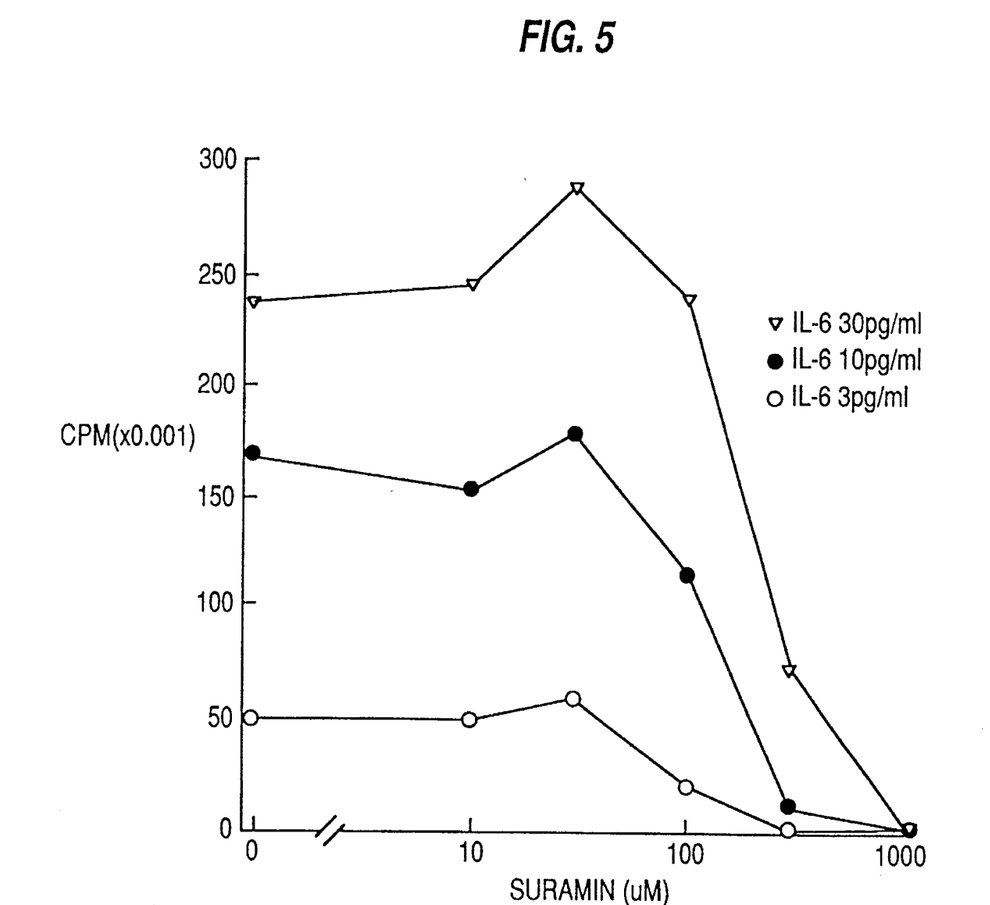
FIG. 5 sets forth the inhibition of bioactivity of IL-6 with the use of suramin.

Increasing amounts of suramin were preincubated with various dosages of IL-6 as indicated in FIG. 5. A standard proliferation assay, Strassmann et al., J. Immunol., 147:1279–1285 (1991), was conducted using 96 well plates The medium used was RPMI with 10% fetal calf serum B-9 cells were added and were cultured for 3 days. The extent of proliferation of B-9 cells was determined by the incorporation of radioactive thymidine as described in Strassmann et al., J. Clin. Invest., 89, pp. 1681–84 (May 1992). As set forth in FIG. 5, suramin inhibits the bioactivity of IL-6 in-vitro which was shown to be an important mediator of cachexia in the C-26 tumor model. (See Strassmann et al., J. Clin. Invest., 89, pp. 1681–84 (May 1992), incorporated herein by reference.)

EXAMPLE 6

This experiment analyzed whether suramin inhibits IL-6 bioactivity by interfering with binding to the IL-6 receptor. Into eighteen test tubes was placed U266 indicator cells (obtained from ATCC), a binding buffer, made up of RPMI medium, 0.1 mg BSA and 25 uM Hepes, and 100,000 cpm (0.8 ng) of $^{125}$I-IL-6. The tubes were divided into six groups of three tubes each and received suramin as follows: group 1 had 300 uM suramin; group 2 had 100 uM suramin; group 3 had 30 uM suramin; group 4 had 10 uM suramin; and group 5 had no suramin, but only medium (control for maximal binding). In addition, group 6 received excess unlabeled IL-6 without suramin for use in determining the background of binding in this assay.

Figure 6:
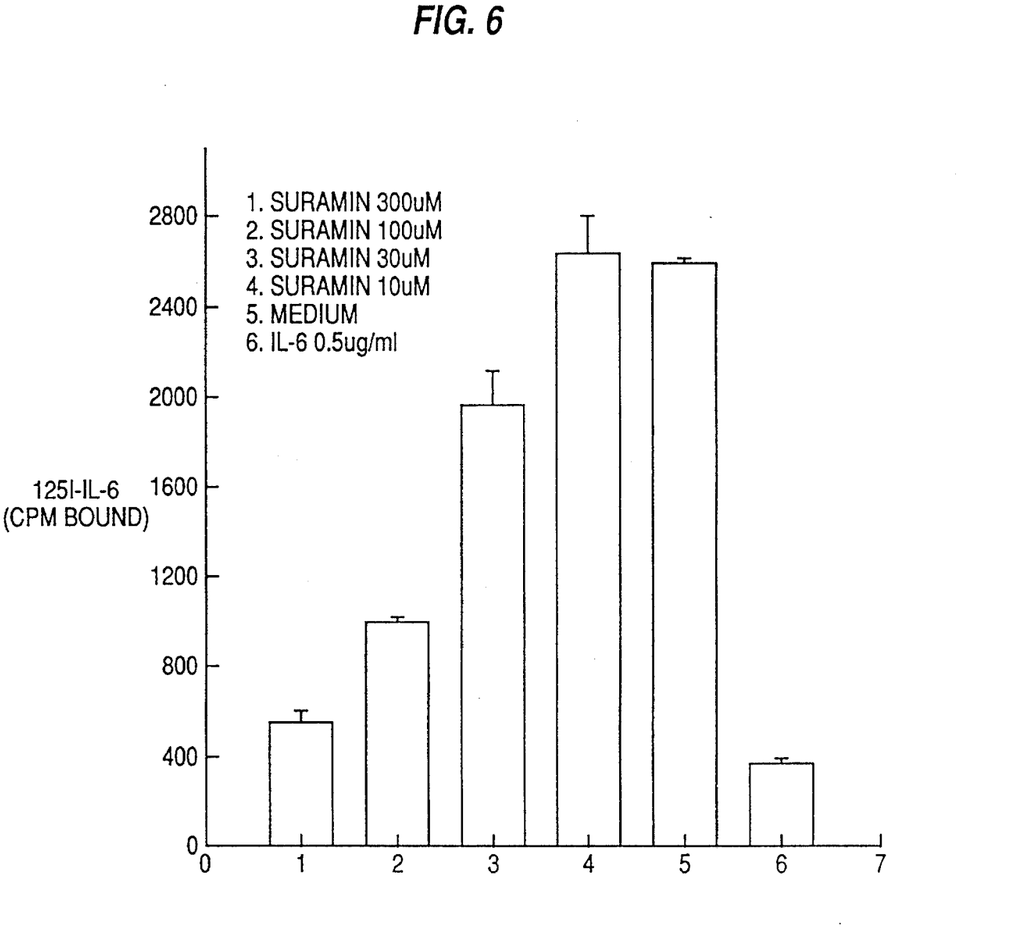
FIG. 6 sets forth the prevention of the binding of IL-6 to human myeloma cells with the use of suramin in a dose dependent manner.

After 90 minutes of incubation at 4° C. and the centrifugation of cells on oil (a standard radioreceptor assay) Strassmann, J. Immunol., 147:1279–1289 (1991), the amount of radioactivity bound to the cells was determined. As can be seen in FIG. 6, suramin prevents binding of the IL-6 to the U266 cells in a dose dependent manner. Also, the addition of increasing amounts of suramin prevented the binding of radioactive IL-6 to U266 human myeloma indicator cells in vitro as reflected in the results set forth in FIG. 6. Together, these results suggest that suramin prevents the binding of IL-6 to cell surface receptors and therefore inhibits IL-6 bioactivity.

EXAMPLE 7

The ability to prevent binding of IL-6 in vivo was analyzed as follows. Eight mice received 5.0 mg/mouse of suramin intravenously and eight other mice received 0.2 ml PBS/mouse intravenously 0.5 hour. Thereafter, all sixteen of the mice received an injection of 300,000 cpm (2.4 ng) of $^{125}$I-IL-6. Four mice from each group were sacrificed 30 minutes after receiving the $^{125}$I-IL-6 and the remaining four mice from each group were sacrificed 60 minutes after receiving the $^{125}$I-IL-6. The liver, kidney, and spleen were removed and measured for radioactivity (cpm). As can be seen in Table 2, suramin injected mice had approximately 50% less radioactivity measured in the liver, indicating that suramin may prevent binding of radioactive IL-6 to the liver. In addition, suramin may accelerate clearance of IL-6 from the body as indicated by the increase of radioactive IL-6 present in the kidney. These results indicate that suramin prevents the binding of IL-6 to the liver and may therefore inhibit IL-6 pathology (for example, cachexia) in vivo.

TABLE 2

Modulation of $^{125}$I-IL-6 Sequestration by Suramin In Vivo

| Treat-ment | 30 minutes | | 60 minutes | |
|---|---|---|---|---|
| | PBS | Suramin | PBS | Suramin |
| Expt. 1 | | | | |
| Liver | 16583 ± 323 | 8385 ± 1525 | 7899 ± 168 | 4275 ± 91 |
| Kidney | 19283 ± 530 | 70151 ± 125 | 9975 ± 532 | 36595 ± 1760 |
| Spleen | 1059 ± 20 | 1347 ± 295 | 728 ± 5 | 630 ± 6 |
| Expt. 2 | | | | |
| Liver | 15002 ± 198 | 9277 ± 235 | 8589 ± 249 | 5512 ± 379 |
| Kidney | 19953 ± 7 | 57287 ± 2849 | 7569 ± 30 | 38254 ± 466 |
| Spleen | 1098 ± 15 | 1306 ± 4 | 549 ± 10 | 631 ± 25 |

Results are expressed as mean cpm ± 0.5 range of 2 mice per point.
Liver radioactivity is expressed as cpm/gm.
PBS (0.2 ml) or Suramin (5 mg/mouse) was injected 0.5 hour before injection of 300,000 cpm (2.4 ng) of $^{125}$I-IL-6.

EXAMPLE 8

The same procedures set forth in Example 5 was followed except that a different sulfate-containing compound, Pentosan polysulfate, was used. As set forth in Table 3, Pentosan poly sulfate prevented the proliferation of B-9 cells in response to

TABLE 3

Pentosan polysulfate inhibits proliferation of B-9 cells in response to IL-6.

| Pentosan polysulfate | IL-6 added (pg/ml) | | | |
|---|---|---|---|---|
| | 30 | 10 | 3 | 1 |
| 0 | 133625 | 115525 | 39947 | 10690 |
| 300 μM | 60287 | 11456 | 2648 | 1567 |
| 1000 μM | 26727 | 3586 | 1062 | 795 |

Results are expressed in cpm of $^3$H-thymidine.

EXAMPLE 9

The same procedure set forth in Example 6 was followed, except that Pentosan polysulfate was used instead of Suramin. As set forth in Table 4, increasing amounts of Pentosan polysulfate inhibited the binding of radioactive IL-6 to U266 human myeloma cells.

TABLE 4

Pentosan polysulfate inhibits binding of radioactive IL-6 to U266 cells.

| Addition to radioreceptor assay | cpm $^{125}$I-IL-6 bound to U266 cells |
|---|---|
| medium | 4072 |
| pentosan polysulfate | |
| 300 μM | 2003 |
| 30 μM | 2575 |

TABLE 4-continued

Pentosan polysulfate inhibits binding of radioactive IL-6 to U266 cells.

| Addition to radioreceptor assay | cpm $^{125}$I-IL-6 bound to U266 cells |
|---|---|
| 3 μM | 3000 |
| hIL-6 270 ng/ml | 1416 |

EXAMPLE 10

The same procedure set forth in Example 5 was followed except in this example, Dextran sulfate and Dextran, were used instead of Suramin. As set forth in Table 5, Dextran sulfate prevented the proliferation of B-9 cells in response to IL-6. Also, as set forth in Table 5, Dextran did not prevent the proliferation of B-9 cells in response to IL-6. These combined results suggest that the sulfate in the Dextran sulfate is an active ingredient which prevented the proliferation of B-9 cells in response to IL-6.

TABLE 5

Dextran sulfate but not dextran inhibit IL-6 dependent proliferation of B-9 cells.

| IL-6 | 30 pg/ml | 10 pg/ml | 3 pg/ml |
|---|---|---|---|
| No Compound | 254937 | 143846 | 32373 |
| Dextran sulfate | | | |
| 300 μM | 112835 | 16573 | 2461 |
| 100 μM | 150233 | 31678 | 8075 |
| 30 μM | 204155 | 68066 | 7603 |
| Dextran | | | |
| 300 μM | 245701 | 140903 | 27015 |
| 100 μM | 230321 | 136191 | 29577 |
| 30 μM | 231856 | 143003 | 24007 |

Results are expressed in cpm of 3H-thymidine incorporation.

Other embodiments of the present invention will be apparent to those skilled in the art from a consideration of the specification and practice of the present invention disclosed herein. It is intended that the present specification and examples be considered as exemplary only, with the true scope and spirit of the present invention being indicated by the following claims.

What is claimed is:

1. A method to mitigate or eliminate weight loss due to wasting of body fat and muscle caused by a mediator in a patient comprising the step of administering to said patient a sulfate-containing compound in an amount effective to mitigate or eliminate said weight loss, wherein said sulfate-containing compound is suramin and wherein said mediator is not treated.

2. The method of claim 1, wherein said mediator is tumor necrosis factor.

3. The method of claim 1, wherein said mediator is cancer.

4. The method of claim 1, wherein said mediator is an infection by gram-negative or gram-positive bacteria.

5. The method of claim 1, wherein said mediator is an infection due to gram-negative cocci.

6. The method of claim 1, wherein said mediator is carcinoma or leukemia.

* * * * *